Figure 1:
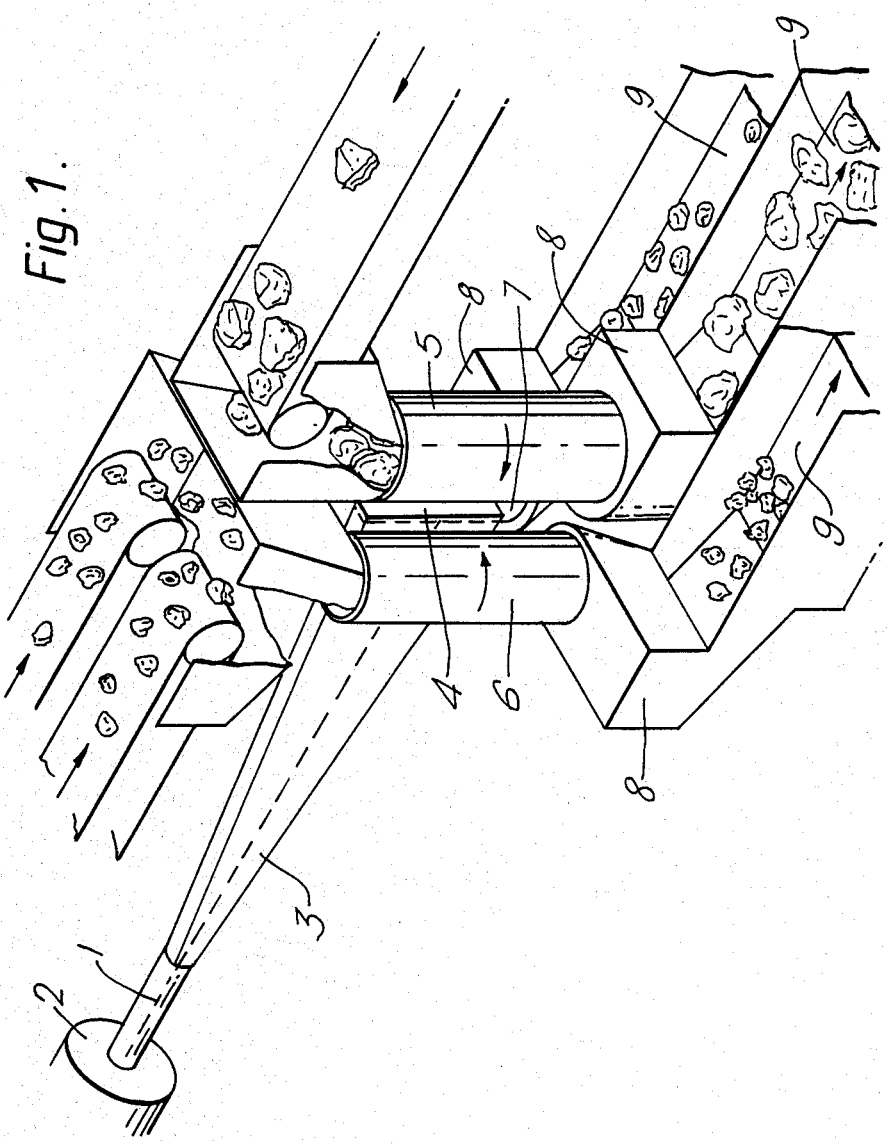

United States Patent [19]

Clayton et al.

[11] Patent Number: 4,830,193
[45] Date of Patent: May 16, 1989

[54] GOLD ORE SORTING

[75] Inventors: Colin G. Clayton, Abingdon; Ramon Spackman, Upton, both of England

[73] Assignee: United Kingdom Atomic Energy Authority, London, England

[21] Appl. No.: 140,865

[22] Filed: Dec. 29, 1987

Related U.S. Application Data

[63] Continuation of Ser. No. 382,686, May 27, 1982, abandoned.

[30] Foreign Application Priority Data

Jun. 10, 1981 [GB] United Kingdom ................ 8117854

[51] Int. Cl.$^4$ ......................... B07C 5/02; B07C 5/346
[52] U.S. Cl. ..................................... 209/3.1; 209/589; 376/159
[58] Field of Search .................................. 209/3.1–3.3, 209/44.1, 509, 552, 576, 589, 912; 250/358.1, 359.1, 390, 391, 393, 432 R, 434, 435; 376/159, 162

[56] References Cited

U.S. PATENT DOCUMENTS

| | | | |
|---|---|---|---|
| 2,587,686 | 3/1952 | Berry | 209/557 X |
| 2,707,555 | 5/1955 | Gaudin | 209/589 X |
| 2,983,834 | 5/1961 | Reiffel | 376/144 |
| 3,053,388 | 9/1962 | Tittle | 250/359.1 X |
| 3,124,679 | 3/1964 | Tittman et al. | 250/390 X |
| 3,215,836 | 11/1965 | Frey, Jr. | 376/114 |
| 3,216,568 | 11/1965 | Jacob et al. | 209/912 X |
| 3,237,765 | 3/1966 | Gaudin et al. | 209/589 |
| 3,299,268 | 1/1967 | Muto et al. | 250/390 X |
| 3,437,808 | 4/1969 | Mott et al. | 209/576 X |
| 4,021,669 | 5/1977 | Valentine et al. | 209/589 X |
| 4,028,267 | 6/1977 | Christell et al. | 250/359.1 |
| 4,340,443 | 7/1982 | Clayton et al. | 376/159 |

FOREIGN PATENT DOCUMENTS

| | | | |
|---|---|---|---|
| 1131187 | 9/1982 | Canada | 209/589 |
| 0059033 | 9/1982 | European Pat. Off. | 209/589 |
| 0941301 | 11/1963 | United Kingdom | 209/589 |

Primary Examiner—Robert B. Reeves
Assistant Examiner—Edward M. Wacyra
Attorney, Agent, or Firm—William R. Hinds

[57] ABSTRACT

A gold sorting plant in which the gold content of lumps of ore is measured by means of a neutron activation analytical technique. Separate lumps of gold ore are graded in two sizes which are presented to an irradiator such as to irradiate them uniformly. The energized lumps of ore are conveyed to an analyzer/sorter station where the intensity of γ-rays having an energy of 297 KeV from each lump of ore is measured, and it is accepted or rejected for further processing. Various forms of irradiator and analyzer/sorter are described.

7 Claims, 2 Drawing Sheets

GOLD ORE SORTING

This application is a continuation of Ser. No. 382,686, filed May 27, 1982, now abandoned.

The present invention relates to the measurement of the gold content of gold-bearing ores, and the sorting of individual lumps of gold-bearing ore according to their gold content.

A practicable gold sorting plant needs to be able to process several tons of ore an hour. Hence it must utilise a very rapid analytical technique. A suitable analytical technique is neutron activation analysis, using the reaction $^{197}Au(n,n'\gamma)^{197m}Au$ to activate the gold present in each lump of ore, and then measuring the intensity of the resultant $\gamma$-rays having an energy of 297 keV and a half-life of 7.8 seconds. It is necessary to ensure that there is a high yield of $^{197m}Au$ nuclei and that the lumps of ore are activated uniformly, that is to say, every lump of ore of the same gold grade (total gold content/mass) has the same specific activity (total mass of $^{197m}Au$ nuclei/mass).

According to the present invention there is provided an apparatus for sorting lumps of gold-bearing ore according to their gold content, including means for irradiating the lumps of ore with neutrons, means for measuring the intensity of $\gamma$-rays having an energy of 297 KeV arising from the nuclear reaction $^{197}Au(nn,n'\gamma)^{197m}Au$, and means responsive to the measured $\gamma$-ray intensity from a given lump of ore to sort that lump of ore from other lumps of ore, wherein the means for irradiating the lumps of ore with neutrons comprises a high voltage accelerator neutron tube adapted to produce at least $10^{10}$ neutrons per second with an energy less than 4.5 MeV, and one or more rotatable cylinders surrounding the neutron producing target with their axes parallel thereto, and means for rotating the cylinders at a speed such that each lump of ore makes at least one complete circuit of a helical path through the neutron field during its passage through its relevant cylinder.

Figure 2:
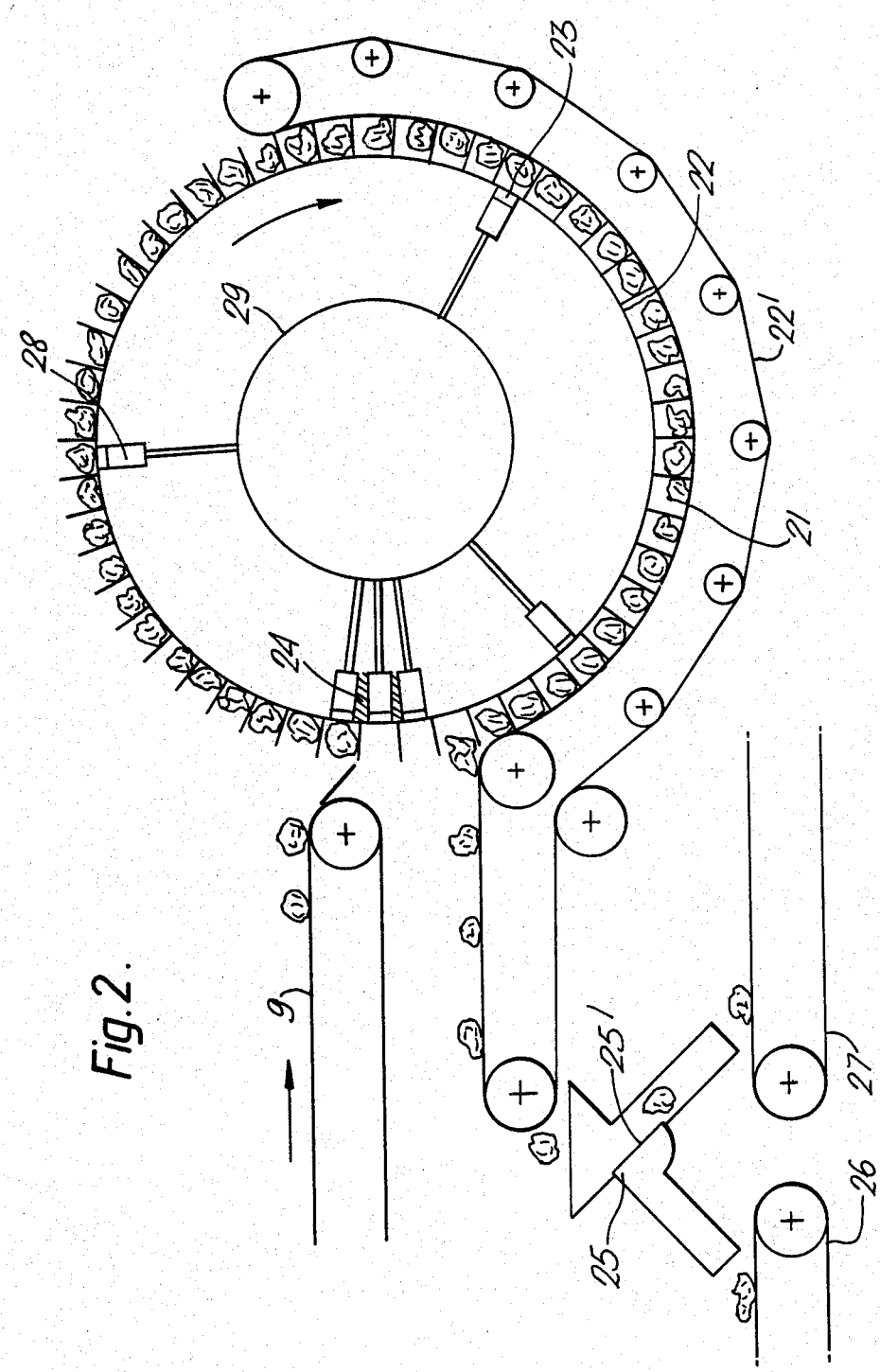

The invention will now be described, by way of example, with reference to the accompanying drawings, in which FIG. 1 is a diagrammatic representation of part of an ore sorting apparatus incorporating the invention, FIG. 2 is a diagrammatic representation of another part of the sorting apparatus embodying the invention.

Referring to FIG. 1, a beam of deuterons 1 from a high voltage accelerator 2 passes along a drift tube 3 and impinges on a target 4 made of titanium deuteride ($TiD_2$). Positioned symmetrically about the deuteron drift tube 3 and target 4 are three vertical cylinders, 5, 6 and 7, respectively, which are arranged to be rotated about their longitudinal axes by means of electric motors, which are not illustrated. The cylinder 5, has its axis of rotation on the line of flight of the deuteron beam 1. The cylinder 5 has a diameter which is approximately 1.5 times that of the cylinders 6 and 7. Prior to their arrival at the cylinders 5, 6 and 7, lumps of ore are sorted into two sizes, the larger ones being directed into the cylinder 5 and the smaller ones into the cylinders 6 and 7.

Fifty percent of the throughput of the plant passes through the cylinder 5 and twenty five percent passes through each of the cylinders 6 and 7. The rates of feed and withdrawal from the cylinders 5, 6 and 7 are arranged to be such that the linear speed of the lumps of rock through the cylinders 5, 6 and 7 is so matched to the rate of rotation of the cylinders 5, 6 and 7, that each lump of ore traverses the high intensity region of the neutron field the same integral number of times. For example, if the length of the target 4 is 11 cm (parallel to the axes of the cylinders 5, 6 and 7) a linear velocity of the lumps of ore through the cylinders 5, 6 and 7 of 5.5 cm/s results in two complete passages of the lumps of ore through the neutron field.

A convenient way of controlling the outlet of the lumps of ore from the cylinders 5, 6 and 7, which is a vital factor in maintaining a uniform level of activation of the gold in the lumps of ore, is to use a vibrator 8 at the outlet end of each of the cylinders 5, 6 and 7.

Upon leaving the cylinders 5, 6 and 7, the irradiated lumps of ore are carried on three conveyor belts 9 to a detector/sorter station one channel of which is illustrated in FIG. 2. In fact, to facilitate the rapid measurement of the activity of the irradiated lumps of ore, which is necessary because of the short half-life of $^{197m}Au$, twelve such channels are used, four being served by each conveyor belt 9. Each measurement channel consists of a rotating wheel 21 the periphery of which is divided into fifty compartments 22. Each compartment 22 has associated with it a scintillation radiation detector 23. The radiation detectors 23 are separated by lead screens 24 so that a lump of ore in one compartment 22 cannot affect the measurement of the activity of another lump of ore in another compartment 22. Lead shields also are interposed between each of the wheels 21. The lumps of ore are held close to the detectors 23 by means of a pressure belt 22' which serves also as a conveyor belt conveying lumps of ore after they have been analysed to an accept/reject gate 25. The accept/reject gate 25 feeds two further conveyor belts 26 and 27, respectively.

Each detector 23 has associated with it an electronic measuring unit 28, the output signals from which are fed to a slip ring 29 at the centre of the wheel 21, whence they are taken to an electro-magnetic actuator, not shown, for a simple gate flap 25' in the accept/reject gate 25.

We claim:

1. Apparatus for sorting lumps of goldbearing ore according to their gold content, including means for irradiating the lumps of ore with neutrons, means for measuring the intensity of $\gamma$-rays having an energy of 297 KeV arising from the nuclear reaction $^{197}Au(nn,n'\gamma)^{197m}Au$, and means responsive to the measured $\gamma$-ray intensity from a given lump of ore to sort that lump of ore from other lumps of ore, the improvement wherein the means for irradiating the lumps of ore with neutrons comprises a high voltage accelerator neutron tube having a vertically positioned linear neutron producing target adapted to produce at least $10^{10}$ neutrons per second with an energy less than 4.5 MeV, and means for presenting the individual lumps of ore to be irradiated by neutrons, said last mentioned means comprising at least one cylinder mounted with its longitudinal axis parallel to the neutron producing target, means for rotating the cylinder about its longitudinal axis, and means for causing the lumps of ore to pass through the cylinder at a rate such that each lump of ore makes at least one complete circuit of a helical path through the neutron field during its passage through the cylinder.

2. Apparatus according to claim 1, wherein the means for presenting the individual lumps of ore to be irradiated by neutrons comprises three said cylinders disposed in parallel relationship at the vertices of an isosceles triangle with one cylinder having a diameter approximately 1.5 times that of the other two, the cylinders being so positioned that the large cylinder has its longitudinal axis on the line of flight of the beam of particles and perpendicular thereto and the smaller cylinders are disposed symmetrically about the line of flight of the particles so as to enclose the neutron producing target, means for directing lumps of ore having a size above a predetermined value to the large cylinder and half the quantity of lumps of ore smaller than the given size to each of the smaller cylinders, and means for rotating the cylinders at speeds such that each lump of ore passes through the high intensity region of the neutron field the same number of times during its passage through a cylinder.

3. Apparatus according to claim 2, wherein the speed of passage of the lumps of ore through the cylinders is controlled by vibrators at the outlets of the cylinders.

4. Apparatus according to claim 1, wherein the means for measuring the intensity of $\gamma$-rays having an energy of 297 KeV includes a plurality of receptacles, each adapted to receive a single lump of ore and bring it into juxtaposition with a $\gamma$-ray detector which is responsive to the said $\gamma$-ray.

5. Apparatus according to claim 4, wherein the receptacles are disposed around the perihery of at least one rotatable member.

6. Apparatus according to claim 5, wherein each receptacle has an associated $\gamma$-ray detector.

7. Apparatus according to claim 4, wherein there is included means for releasing each lump of ore from its receptacle at an outlet station at which there is situated a selector which is arranged to operate in response to a signal received from the $\gamma$-ray detector relating to each lump of ore as it is released so as to accept or reject that lump of ore for processing.

* * * * *